United States Patent [19]
Lentz et al.

[11] Patent Number: 5,851,229
[45] Date of Patent: Dec. 22, 1998

[54] BIORESORBABLE SEALANTS FOR POROUS VASCULAR GRAFTS

[75] Inventors: David J. Lentz, Randolph; Gary L. Loomis, Morristown; Antonio Moroni, Morris Plains; Jennifer DePreker, Rochelle Park, all of N.J.

[73] Assignee: Meadox Medicals, Inc., Oakland, N.J.

[21] Appl. No.: 713,801

[22] Filed: Sep. 13, 1996

[51] Int. Cl.[6] ................................. A61F 2/06; A61F 2/04
[52] U.S. Cl. ................................. 623/1; 623/11; 623/12; 623/8
[58] Field of Search .................... 623/1, 11, 12, 623/8, 17; 606/194, 195, 151–158; 600/36

[56] References Cited

U.S. PATENT DOCUMENTS

| | | |
|---|---|---|
| 4,167,045 | 9/1979 | Sawyer . |
| 4,371,711 | 2/1983 | Mano ................................. 623/1 |
| 4,416,814 | 11/1983 | Battista . |
| 4,704,131 | 11/1987 | Noishiki et al. ..................... 623/1 |
| 4,787,900 | 11/1988 | Yannas ................................. 623/1 |
| 5,028,597 | 7/1991 | Kodama et al. ..................... 623/1 |
| 5,100,783 | 3/1992 | Dean Jr. et al. . |
| 5,135,755 | 8/1992 | Czech et al. . |
| 5,209,776 | 5/1993 | Bass et al. . |
| 5,336,501 | 8/1994 | Czech et al. . |
| 5,360,828 | 11/1994 | Morrison . |
| 5,415,619 | 5/1995 | Lee et al. . |
| 5,584,875 | 12/1996 | Duhamel et al. . |

FOREIGN PATENT DOCUMENTS

| | | |
|---|---|---|
| 0 230 635 | 8/1987 | European Pat. Off. . |
| 0 271 216 | 6/1988 | European Pat. Off. . |
| 0 486 294 | 5/1992 | European Pat. Off. . |
| WO 92/09311 | 6/1992 | WIPO . |
| WO 95/01190 | 1/1995 | WIPO . |

OTHER PUBLICATIONS

Biodegradable Hydrogels for Drug Delivery by Kinam Park, Waleed S.W. Shalaby and Haesun Park (1993).

*Primary Examiner*—Debra S. Brittingham
*Attorney, Agent, or Firm*—Hoffmann & Baron, LLP

[57] ABSTRACT

A bioresorbable sealant composition useful for impregnating implantable soft-tissue prostheses includes at least two polysaccharides in combination to form a hydrogel or sol-gel. The sealant compositions may optionally include a bioactive agent and/or be cross-linked subsequent to application of these compositions to the substrate surface.

19 Claims, No Drawings

BIORESORBABLE SEALANTS FOR POROUS VASCULAR GRAFTS

FIELD OF INVENTION

The present invention generally relates to sealants for porous implantable devices. More particularly, the present invention is directed to porous implantable vascular grafts impregnated with hydrogel or sol-gel mixtures of polysaccharides that render such grafts blood-tight. Another aspect of the invention is directed toward providing timed-released delivery of therapeutic agents impregnated within the interstitial spaces of such grafts. Methods of providing these grafts are also provided.

BACKGROUND OF THE INVENTION

In general, it is important that implantable tubular devices designed to carry fluids be fluid-tight and nonthrombogenic while at the same time accommodating to tissue ingrowth. This is especially true for implantable vascular prostheses. In order to accommodate tissue ingrowth, such a prosthesis may be porous. Most textile porous endoprostheses and grafts, however, are not naturally blood-tight and, unless preclotted or coated with a biocompatible water-tight coating, substantial bleeding may occur through the walls of the graft. Accordingly, a balance must be struck between maintaining a blood-tight surface and promotion of tissue ingrowth into such vascular grafts. In particular, vascular grafts made of porous materials must be substantially blood-tight during the initial introduction of the vascular graft into the body of a patient in order to reduce blood loss to the patient. As the graft site heals, however, tissue ingrowth into the graft must be encouraged. Thus, it is desirable to have graft materials which are both blood-tight and yet encourage tissue ingrowth. Such characteristics, however, require the graft to have two different physical structures.

For example, vascular graft materials that promote tissue ingrowth and healing must be porous enough to allow cells and nutrients to migrate into the graft. Such cellular ingrowth is vital for the long term patency of the graft. Nylon, polyester, polytetrafluoroethylene (PTFE), polypropylene, polyurethane, polyacrylonitrile, etc. are known in the art as materials for making such vascular grafts. PTFE and polyester are widely used today because they are inert materials that have low thrombogenicity in the body. In particular, polyethyleneterephthalate is most commonly used in making textile vascular grafts and endoprostheses.

For the surgeon, the porosity of such graft materials is an essential factor to consider. In particular, the porosity of such materials contributes to the long-term patency and overall performance of a graft. In addition, ease of handling, anastomosis and flexibility usually increase as the porosity of a graft material increases. Also, the healing process, i.e., the ability of connective tissue cells to infiltrate the graft increases as the porosity of the graft material increases.

The ability of such porous graft materials to promote tissue ingrowth etc., however, comes at a price. Untreated, such a graft is not blood-tight. Thus, when the graft is implanted, bleeding through the pores in the surface of the graft is a significant problem. Alternative methods have been developed for reducing blood loss through leakage of the vascular graft. For example, less porous materials have been used as vascular grafts. Such materials, however, suffer from their inability to support endothelialization of the lumen and tissue ingrowth into the graft. Accordingly, such textile graft materials are not practical because their patency is short-lived.

Alternatively, porous vascular graft materials have been pretreated with blood prior to introduction of the graft into the body. Such a pretreatment introduces clotting factors throughout the graft that help to reduce bleeding during surgery by causing blood to become clotted before significant loss of blood to the patient occurs. Generally, these grafts are immersed in, or flushed with, fresh blood of the patient in order to preclot the surfaces of the graft. These methods are limited because they are time consuming, require blood transfusions from the patient, and increase the amount of blood loss from the patient. Thus, such methods are not available in emergency medical situations where the patient has lost a large amount of blood or where time is a critical factor. In addition, such methods cannot be used effectively with patients who are taking anticoagulants, such as heparin or warfarin.

A considerable amount of research has centered around developing materials that are initially blood-tight and then gradually become more porous in order to facilitate healing and tissue ingrowth into the implanted graft. Much of this research has focused on coating the surfaces of porous graft materials with extracellular matrix (ECM) proteins in order to render such graft materials blood-tight, but which, over time biodegrade and promote tissue ingrowth into the graft. For example, collagen, albumin, gelatin, elastin, and fibrin have all been used as bioresorbable sealants for porous vascular grafts.

In addition, gels, hydrogels and sol-gels have also been described as biocompatible, biodegradable materials. A gel is a substance with properties intermediate between the liquid and solid states. Gels deform elastically and recover, yet will often flow at higher stresses. They have extended three-dimensional network structures and are highly porous. Accordingly, many gels contain a very high proportion of liquid to solid. The network structures can be permanent or temporary and are based on polymeric molecules, basically formed from a colloidal solution on standing. Thus, a hydrogel may be described as a gel, the liquid constituent of which is water. By way of contrast, a sol is a colloidal solution, i.e., a suspension of solid particles of colloidal dimensions in a liquid. See, Larouse Directory of Science and Technology 470, 543 (1995).

By way of example, U.S. Pat. No. 5,209,776 ('776 patent) issued to Bass et al. discloses a composition for bonding separated tissues together or for coating the surface of tissues or prosthetic materials in order to form a water-tight seal thereon. The composition of the '776 patent includes a first protein component that is preferably a collagen and a second protein-supporting component that can be a proteoglycan, a saccharide or a polyalcohol. In this composition, the second component is adapted to support the first component by forming a matrix, sol or gel with the first component. Thus, the matrix, sol or gel formed is a hybrid composition that includes a protein component and a protein-supporting component that can be a protein, a saccharide or a polyalcohol. The protein component provides the sealing or bonding function, while the protein-supporting component forms a supporting matrix for the protein.

In another example, U.S. Pat. Nos. 5,135,755 and 5,336,501 both issued to Czech et al. disclose hydrogels that may be used as wound secretion absorbers or incorporated into wound dressings for absorbing wound secretions. The hydrogel composition of these inventions include 20–70% of at least one multivalent alcohol, for example glycerol, 10–35% of at least one natural biopolymer thickener agent, 0.05–10% of a cross-linking agent and 0–50% of water or physiological saline.

The gel or hydrogel described in these patents can be gelatin alone or gelatin in combination with a polysaccharide, particularly an alginate. Thus, the hydrogel of these patents is a protein hydrogel or a protein-polysaccharide hybrid hydrogel. In addition to gelatin, collagens and pectins are also preferred protein components in the hydrogel materials of these patents. These patents all require conventional protein materials to provide the sealing function and the hydrogels are used as carriers for the proteins.

Such hybrid coating compositions described in the Bass and Czech patents however, are not easily manufactured. For example, the protein components of the hybrid coating compositions can become denatured during the manufacturing, sterilizing or storing of the hydrogel coated material (wound dressing as in Czech or an implantable device as in Bass). Once denatured, these hybrid coating compositions can lose their ability to function. Another problem with such hybrid coating compositions is that the surface of the substrate material, e.g., wound dressing or implantable device, must be pretreated with, for example, plasma, in order to effectively bind such compositions to the surface of, for example, a vascular graft. In addition, such hybrid compositions are deposited as coatings on the surface of a substrate material. Such surface coatings are limited in that they are readily accessible to the body's degradative enzymes and thus are swiftly degraded.

In an attempt to alleviate the problems incident with such protein or protein hybrid coatings, U.S. Pat. No. 5,415,619 issued to Lee et al. ('619 patent) describes a method of rendering a porous vascular graft blood-tight by impregnating the surface thereof with a polysaccharide or polysaccharide derivative. Accordingly, the '619 patent uses the word "impregnate" to mean physically adsorbing or chemically binding the polysaccharides to the surface of a graft. Although this method alleviates the problem of protein denaturation during the manufacturing, sterilizing and storing of, for example, a vascular graft, the surface of such a graft must be chemically or physically altered in order to bind the polysaccharide coating to the surface thereof. For example, the '619 patent describes chemically oxidizing the surface of a porous vascular graft with a solution of sulfuric or perchloric acid prior to impregnating the surface of the graft with a polysaccharide solution. Alternatively, the '619 patent describes physically altering the surface of such a graft by pretreatment with plasma or corona discharge. In either case, the methods described in the '619 patent add additional unnecessary steps to such a process by chemically or physically pretreating the surface of such vascular grafts.

Accordingly, it would be desirable to provide an improved bioresorbable sealant for porous implantable prostheses, such as vascular grafts, that renders the porous prosthesis blood-tight upon introduction into the body and that is bioresorbable over time such that tissue ingrowth is promoted. In particular, it would be desirable to provide an improved bioresorbable sealant for a porous vascular graft that renders such a graft blood-tight and that does not require physical or chemical modification of the surface of such a graft prior to incorporation of the sealant.

SUMMARY OF THE INVENTION

In accordance with the present invention, an improved bioresorbable sealant composition for implantable prostheses is provided. In particular, the bioresorbable sealant composition includes the combination of at least two polysaccharides which form a hydrogel that imparts a substantially blood-tight barrier to the implantable prostheses. Preferably the prosthesis is a soft tissue prostheses used in the vascular system, such as a vascular graft or endoprosthesis. Other tubular prostheses or soft-tissue prostheses such as surgical mesh or hernia plugs are also contemplated.

The implantable prosthesis is preferably made from a synthetic textile material that is woven or knitted into a tubular prosthesis. Useful materials include for example, polyester, poly(tetrafluoroethylene), nylon, polypropylene, polyurethane and polyacrylonitrile, among others. In addition to knitted or woven textile fabrics, the prosthesis may be formed from extrusion and expansion techniques, such as with expanded poly(tetrafluoroethylene) (ePFTE). Composites of these materials, as well as others, are also contemplated.

In the present invention, useful polysaccharides include algin, carboxymethyl cellulose, carrageenan, including carrageenan type I, carrageenan type II, carrageenan type III, and carrageenan type IV, furcellaran, agarose, guar, locust bean gum, gum arabic, hydroxyethyl cellulose, hydroxypropyl cellulose, methyl cellulose, hydroxyalkylmethyl cellulose, pectin, partially de-acetylated chitosan, starch and starch derivatives including, amylose and amylopectin, xanthan, casein, polylysine, hyaluronic acid and its derivatives, heparin, their salts, and mixtures thereof.

As previously mentioned, the present invention requires the combination of at least two polysaccharides, or a polysaccharide and a protein to form a hydrogel. Numerous combinations of polysaccharides may be used in this invention, such as, for example: alginic acid/pectin, alginic acid/chitosan, carrageenan type I/locust bean gum, carrageenan type I/pectin, carrageenan type II/locust bean gum, carrageenan type II/pectin, carrageenan type I/guar gum, carrageenan type IV/locust bean gum, locust bean gum/xanthan, guar gum/locust bean gum, guar gum/xanthan, and agar/guar gum. Preferred combinations of polysaccharides which form a hydrogel include carrageenan type II with $Ca^{+2}$ ion and/or locust bean gum, or carrageenan type IV, $Ca^{+2}$ with or without locust bean gum. Other preferred combinations include purified agarose/guar gum, as well as chitosan/guar gum. Because natural polysaccharides are constantly being isolated and characterized, and new polysaccharides may be produced by molecular biology techniques, other such polysaccharides are useful in the present invention.

The present invention also contemplates incorporating a therapeutic or bioactive agent into the hydrogel. In this way, the hydrogel controllably releases the therapeutic agent while the hydrogel is biodegraded or bioresorbed. One particularly useful class of therapeutic agents is the anticoagulants. As used herein, the anticoagulant agent may include any agent useful for such purposes, but among those currently known as being useful are heparin, sulfated polysaccharides, prostaglandin, urokinase, hirudin streptokinase, their pharmaceutical salts and mixtures thereof. Heparin is preferred because it is a polysaccharide and is easily incorporated into a hydrogel. Furthermore, combinations of heparin/chitosan are also known to form gels when combined as shown in Table 2.

In the present invention, the hydrogel formed from combinations of polysaccharides may be cross-linked in order to form a tighter barrier and seal around, e.g., throughout the interstitial spaces of, the porous device.

In another embodiment of the invention, a controlled release material is provided that includes a hydrogel matrix formed from at least two polysaccharides and an anticoagulant agent incorporated within the matrix thereof. This material is impregnated within the interstitial space between the inner and outer surfaces of a porous implantable device.

In yet another embodiment of the present invention, there is provided a sealant for an implantable porous luminal substrate. In this embodiment of the invention, a porous substrate having an inner and an outer surface with interstitial spaces defined therebetween is provided. The sealant of this embodiment includes a hydrogel that includes, in combination, at least two polysaccharides. This sealant fills the interstitial space of the porous substrate and imparts a substantially liquid-tight barrier between the inner and outer surfaces of the porous material. The sealant may also be a sol-gel which includes, in combination, at least two polysaccharides.

In another embodiment of the present invention, the prosthesis includes a tubular member that is impregnated with a hydrogel that is defined by a mixture of a seed gum polysaccharide and a sea weed extract polysaccharide dispersed in a glycerol-water solution. Alternatively, this prosthesis includes a tubular member that is impregnated with a hydrogel that is defined by a mixture of a linear polysaccharide component and a branched polysaccharide component dispersed in a glycerol-water solution.

A method for rendering an implantable porous tubular substrate fluid-tight is also provided. The method includes providing an implantable porous substrate having an inner and an outer surface with an interstitial space defined therebetween; providing a hydrogel or a sol-gel that includes at least two polysaccharides; and impregnating the porous substrate with the hydrogel or sol-gel to render the substrate fluid-tight.

In yet another embodiment of the present invention, there is provided a bioresorbable sealant composition for use in a soft-tissue prosthesis including, in combination, at least two polysaccharides which when mixed together in an aqueous medium form a hydrogel. This hydrogel forms a liquid-tight seal when applied to the prosthesis as a sealant. A controlled-release, bioresorbable sealant composition is also provided whereby in addition to the combination of at least two polysaccharides, there is also included a therapeutic or bioactive agent which is slowly released in the body subsequent to implantation as the sealant gradually bioerodes and tissue ingrowth increases.

Methods of preparing and using the aforementioned sealant compositions and prostheses containing same are also disclosed.

DETAILED DESCRIPTION OF THE INVENTION

While this invention is satisfied by embodiments in many different forms, there will be described herein in detail preferred embodiments of the invention, with the understanding that the present disclosure is to be considered as exemplary of the principles of the invention and is not intended to limit the invention to the embodiments illustrated and described.

The present invention relates to sealant compositions and implantable soft tissue prostheses having such compositions impregnated therein. In particular, the invention relates to hydrogel or sol-gel sealant compositions which include the combination of at least two polysaccharides. The sealant compositions of the present invention form a substantially liquid-tight, i.e., blood-tight seal on porous substrate surfaces, and particularly the luminal surfaces of substrates such as on vascular grafts. These sealant compositions biodegrade over time in order to allow healing and endothelial cell ingrowth.

The implantable soft tissue prostheses of the present invention can be formed of any porous material, including any synthetic or natural polymer material, onto which a hydrogel or sol-gel can effectively adhere. Thus, such porous materials may include polyesters, expanded poly (tetrafluoroethylene), nylons, polypropylenes, polyurethanes, polyacrylonitriles, polyolefins, polycarbonates, highly cross-linked collagens, polylactides, polyglycosides and combinations thereof. Woven or knitted grafts made of such materials may also be used in this invention. In addition, velour or double velour grafts may also be used.

For purposes of this invention, "hydrogel" and "hydrogel matrix" both refer to a polymeric material that swells in water without dissolving and that retains a significant amount of water in its structure. Such a material has properties intermediate between the liquid and solid states. Hydrogels also deform elastically and recover, yet will often flow at higher stresses. Thus, for purposes of this invention hydrogels are water-swollen, three-dimensional networks of hydrophilic polymers.

By way of contrast, a sol-gel is a hydrogel in which part of the structure is, in some way water-soluble. Thus, in a sol-gel system, some portion of the material is water-extractable, although the rate of solubilization may be low. Accordingly, for purposes of this invention, "sealant" or "sealant matrix" both refer to either a hydrogel or a sol-gel composition as described herein.

These sealant matrices can be made more stable by cross-linking the component parts thereof. The sealant matrices of the present invention can be cross-linked in several ways. For example, formation of covalent bonds between one or more of the polysaccharides in the matrix can produce generally irreversible cross-linking. Alternatively, the sealant matrices of the invention can be cross-linked by the formation of ionic bonds in at least one of the polysaccharides. In another example, cross-links may be formed in the sealant matrices of the invention through weaker intermolecular interactions, such as, for example, hydrogen bonding and specific van der Waals interactions. In yet another example of cross-linking in the present invention, a semicrystalline hydrophilic polymer can form a hydrogel when the amorphous regions of such a polymer absorbs water and the water-insoluble crystalline regions (crystallites) act as physical crosslinks.

These sealant cross-linking mechanisms may be either intramolecular or intermolecular. Furthermore, such interactions may occur between two or more polysaccharides or one polysaccharide and one or more other hydrophilic polymers. It is difficult to predict whether a particular combination of polysaccharides when combined under various conditions will form a gel material which is stable under physiological conditions, is compatible with an appropriate plasticizer, and is suitable for rendering an implantable graft blood-tight. Thus, Table I below is exemplary of some the combinations of polysaccharides prepared according to the present invention. These exemplary polysaccharides were evaluated for their abilities to form stable gels in a physiological phosphate buffer at pH 7.2.

TABLE 1

POLYSACCHARIDE GELS

| POLYSACCHARIDE | INSOLUBLE IN BUFFER | COMBINATIONS PREPARED WITH GLYCEROL | IMPREGNATED GRAFT AND POROSITY TESTED |
|---|---|---|---|
| Low Viscosity Alginic Acid + Pectin | No | No | — |
| Med Viscosity Alginic Acid + Pectin | No | — | — |
| High Viscosity Alginic Acid + Pectin | Yes | Yes | — |
| Low Viscosity Alginic Acid + Chitosan | Yes | — | — |
| Med Viscosity Alginic Acid + Chitosan | No | — | — |
| Carrageenan Type I + Locust Bean Gum | Yes | Yes | Yes |
| Carrageenan Type I + Pectin | Yes | Yes | — |
| Carrageenan Type II + Locust Bean Gum | Yes | Yes | Yes |
| Carrageenan Type II + Pectin | Yes | Yes | — |
| 100% Guar Gum | No | Yes | — |
| 100% Locust Bean Gum | No | Yes | — |
| 100% Purified Agar | Yes | Yes | — |
| Guar Gum + Locust Bean Gum | No | Yes | — |
| Guar Gum + Xantham Gum | Yes | Yes | — |
| Xantham Gum + Locust Bean Gum | Yes | Yes | — |
| Purified Agar + Guar Gum | Yes | Yes | Yes |

Accordingly, in the present invention, at least two polysaccharides must be used to define such sealant matrices. In particular, the following list of polysaccharides may be used herein: heparin, algin, carboxymethyl cellulose, carrageenan, including carrageenan type I, carrageenan type II, carrageenan type III, and carrageenan type IV; furcellaran, agarose, guar, locust bean gum, gum arabic, hydroxyethyl cellulose, hydroxypropyl cellulose, methyl cellulose, hydroxyalkylmethyl cellulose, pectin, chitosan; starch and starch derivatives including, amylose and amylopectin; xanthan, their salts, and mixtures thereof. Certain proteins and polyamino acids may also be useful. Such a list is illustrative and should not be construed to limit in any way the scope of the invention.

Plasticizers and softeners may also be used in the present sealant matrices. Examples of such reagents include glycerol, sorbitol and diols, such as, polypropylene glycol; partially esterfied citric acid, such as, mono-ethylcitrates; and lactic acid esters, such as ethyl lactate may also be used in the present sealant matrices. In the present invention, from about 0% to about 70% plasticizer may be used. It is critical, however, to monitor the concentration of plasticizer in a particular sealant. Too much plasticizer can cause a sealant-impregnated graft material to leak. Such plasticizers, used in the proper concentration as indicated above, are beneficial because they increase the softness and flexibility of the impregnated implantable material.

Table 2 below summarizes some of the relevant chemical properties and gel forming abilities of exemplary polysaccharides of the present invention.

TABLE 2

POLYSACCHARIDE PROPERTIES AND GEL FORMING ABILITIES

| POLYSACCHARIDE | PROPERTIES | GEL FORMING ABILITY WITH OTHER MATERIALS | COMMENTS |
| --- | --- | --- | --- |
| Agar | Contains some $SO_3H$ low solubility below 100° C. | Guar gum forms strong rigid gel, resistant to pH changes | Forms strong, rigid gels that melt at high temperatures |
| Algin (salts of alginic acid) | Polyelectrolyte, contains $COO^-$, forms pseudo plastic solutions | polyamino acids, such as, poly(lysine), $Ca^{+2}$ | Elasticity of gels varies with alginate structure |
| Amylose | Forms dispersions in water that undergo retrogradation | — | — |
| Carrageenan, kappa | Polyanion, contains $SO_3H$, Na salt is soluble in cold water, other in hot water. | $K^+$, proteins, such as, k-casein, locust bean gum | Forms firm, rigid gels when cooled |
| Carrageenan, iota | Polyanion, contains $SO_3H$, similar to kappa carrageenan but more soluble | $K^+$, $Mg^{+2}$, $Ca^{+2}$, proteins, k-casein, locust bean gum | Forms elastic, stable, syneresis free gels that are thermally reversible |
| Carrageenan, lambda | Polyanion contains $SO_3H$, the most soluble, non gelling | $K^+$, proteins, milk proteins, locust bean gum | Anticoagulant, induces connective tissue growth |
| Chitosan | Contains $—NH_2$ | Hyaluronic acid, Heparin, Chondroitin Sulfate, Cellulose Sulfate, and Sodium Carboxymethyl Cellulose | Stimulates macrophage growth, anti-infective agent, immuno-enhancer, hemostatic, accelerates wound healing |
| Furcelleran | Polyanion, contains some $SO_3H$, fewer than the carrageenans but more than Agar; forms flexible, opalescent gels. | Locust bean gum, $K^+$, $Ca^{+2}$, milk proteins | properties similar to carrageenan kappa |
| Guar Gum | Nonionic, disperses ad swells in cold or hot water forms high viscosity, cloudy pseudo plastic solutions | Borates, Xanthan Gum, Carrageenans, and Agar | Viscosity increases after being heated; gels are weaker than locust bean gums |
| Gum Arabic | acidic polysaccharide, highly soluble, forms Newtonian solutions with low viscosity, even at low concentrations | Gelatin | Has a protective colloid action |
| Hydroxyethyl Cellulose, Hydroxypropyl Cellulose | Nonionic, both form clear, smooth solutions and impermeable films | Sodium carboxymethyl cellulose | Properties not affected by pH, Newtonian at low shear rates, pseudo plastic at high shear rates |
| Locust Bean Gum | Nonionic, partially soluble in cold water, fully soluble in hot water, delayed viscosity | kappa carrageenan, Furcelleran, xanthan | Viscosity increases after heating above 85° C. |
| Pectin | Soluble in hot water, gels upon cooling | Sugar, $Ca^{+2}$, pH < 3 | Forms pseudo plastic solutions |
| Sodium Carboxymethyl Cellulose | Polyanion, hydrates rapidly to form clear solutions | Casein, Soy Protein, Guar Gum, HPC and Chitosan | — |
| Xanthan Gum | Anionic, forms viscous, strongly | Locust Bean Gum (thermally reversible | Viscosity does not change |

TABLE 2-continued

POLYSACCHARIDE PROPERTIES AND GEL FORMING ABILITIES

| POLYSACCHARIDE | PROPERTIES | GEL FORMING ABILITY WITH OTHER MATERIALS | COMMENTS |
| --- | --- | --- | --- |
| | pseudo plastic solutions | gel), Guar Gum (weak), Methyl Cellulose | significantly with temperature or pH |

As previously stated, the present invention utilizes in combination at least two polysaccharides as component parts of the sealant matrix. Such paired combinations of polysaccharides include, but are not limited to the following combinations: alginic acid/pectin, alginic acid/chitosan, carrageenan type I/locust bean gum, carrageenan type I/pectin, carrageenan type II/locust bean gum, carrageenan type II/pectin, carrageenan type II/guar gum, carrageenan type IV/locust bean gum, locust bean gum/xanthan, guar gum/locust bean gum, guar gum/xanthan, alginic acid/poly lysine, agar/guar gum, proteins and polyamino acids.

It is known that ions, in particular, $K^+$, $Ca^{+2}$, and $Mg^{+2}$ synergistically interact with certain polysaccharides to form gels. Accordingly, sealant impregnated grafts may be contacted with a solution of such ions in order to increase the strength of the gel. In the present invention, the sealant impregnated grafts may be, for example, dipped, steeped, sprayed or otherwise conventionally contacted with a solution of ions, such as for example, $K^+$, $Ca^{+2}$, and $Mg^{+2}$ ions, although other ions may also be useful. Accordingly, the sealant matrices may include for example, carrageenan type II, $Ca^{+2}$ ion and locust bean gum or carrageenan type IV, $Ca^{+2}$ ion and locust bean gum.

In another embodiment of the present invention, an anticoagulant agent or other bioactive agents may be incorporated into the sealant. In this way, as the sealant's polysaccharide matrix biodegrades the bioactive agent, i.e. anticoagulant agent, may be controllably released over time. Thus, the anticoagulant agent augments the sealant's ability to prevent blood leakage through, for example, the walls of a porous vascular graft. In the present invention, the anticoagulant agent may be a prostaglandin, a urokinase, a streptokinase, a sulfated polysaccharide, an albumin, their pharmaceutical salts and mixtures thereof. Other suitable anticoagulant agents may also be used. Preferably, the anticoagulant agent is heparin or its pharmaceutical salt.

As the type and composition of the sealant matrix can vary, so too can the type and structure of the porous implantable material. For example, generally synthetic grafts fall into one of two categories: textile grafts or extrusion grafts. Textile grafts are manufactured out of extruded fibers, such as, for example, Dacron polyester. Such fibers are made into yarns and are then formed into tubular structures by knitting or weaving. Alternatively, extrusion grafts are non-textile grafts manufactured out of polymers, such as, for example, polytetrafluoroethylene, that are extruded and mechanically stretched to produce a microporous tube. In general, non-coated textile grafts have a higher water permeation rate than non-textile extruded grafts. Accordingly, how a graft is manufactured influences its porosity.

For purposes of this invention, "porous" or "porosity" refers to the relative amount of open or interstitial space in the wall of, for example, a vascular graft. The tightness of the weave or knit of a textile graft, or the degree of stretching of an extruded graft influences its porosity. Other factors influencing the porosity of a textile graft include the type of yarn used and knitting or weaving configuration used. For example, graft materials made of texturized fabrics that have additional yarns added thereto give the fabric a plied or napped texture and are called velour (single-sided) or double-velour (double-sided). Traditionally, such velour grafts were less likely to bleed after implantation because they had more surface area and were easier to preclot.

By way of contrast, grafts formed of expanded PTFE (ePTFE) have a fibrous structure which is defined by inter-spaced nodes interconnected by elongated fibrils. The spaces between the node surfaces that are spanned by the fibrils are defined as the internodal distance (IND). The porosity of an ePTFE vascular graft is controlled by varying the IND of the microporous structure of the graft. An increase in the IND within a given structure results in enhanced tissue ingrowth, as well as cell endothelialization, along the inner surface thereof. This tissue ingrowth and endothelialization promotes stability, enhances radial strength and increases the patency of the graft.

Accordingly, either textile or extruded materials may be used in connection with the sealants of the present invention. It is critical, however, that the walls of the intended graft material be sufficiently porous so that the polysaccharide hydrogel or sol-gel can impregnate the interstitial spaces thereof. For purposes of this invention, "impregnate" is intended to mean the partial or complete filling of the interstitial space, e.g., the pores or spaces between the inner and outer surface of, for example, a vascular graft, in order to render such a graft substantially blood-tight.

For purposes of this invention, the specific porosity of a material can be measured with a Wesolowski Porosity tester. With this apparatus, a graft is tied off at one end and the free end is attached to a valve on a porometer so that the graft hangs freely in a vertical position. Then, water is run through the graft for one minute and all the water that escapes from the graft is collected and measured. The specific porosity of the graft is then calculated according to the following formula:

$$P = \frac{V}{A}$$

where V is the volume of water collected in ml/min and A is the surface area of the graft exposed to water in $cm^2$. A specific porosity of $\leq 1.0$ ml/min/$cm^2$ is considered an acceptable amount of leakage for an implantable vascular graft. Accordingly, for purposes of this invention, a substantially blood-tight graft means a graft with a specific porosity, after impregnation with a sealant of the present invention, of $\leq 1.0$ ml/min/$cm^2$.

In yet another embodiment of the present invention, an anticoagulant agent or other bioactive agent dispersed within a controlled release material is impregnated within the interstitial space between the inner and outer surface of a porous implantable device. The controlled release material is a hydrogel matrix containing at least two polysaccharides as described hereinabove. Thus, as the hydrogel is biodegraded by natural enzymes present in the body, the anticoagulant agent is slowly released over time. Accordingly, in addition to imparting a substantially blood-tight seal to, for example, a vascular graft, the hydrogel matrix as it biodegrades, also provides a support structure from which the anticoagulant or bioactive agent is controllably released. In this way, the controlled release of the anticoagulant enhances the ability of this hydrogel composition to prevent blood loss to the patient by coagulating any blood that evades the physical barrier created by the hydrogel.

According to Kinam Park et al., Biodegradable Hydrogels For Drug Delivery (Technomic Publishing Co. 1993), drug release in a hydrogel system is influenced by various formulation variables and/or physiochemical properties of the components in the system. Thus, in addition to polymer degradation, release of the anticoagulant is affected by the physical parameters of the polymer, such as, water content, degree of crosslinking, crystallinity, and phase separation. In addition, the physiochemical properties of the anticoagulant, particularly its solubility in the polymer and aqueous medium and the amount of drug loaded into the hydrogel are also expected to have significant effects on the release characteristics of the drug-polymer composite. Accordingly, the release rate of the anticoagulant agent will vary according to the variables disclosed hereinabove. Providing the appropriate release rate, however, can be achieved by one skilled in the art by adjusting these parameters.

Any conventional method for filling or impregnating the interstitial spaces of the porous substrate can be used. For example, a sealant mixture of the present invention was placed in a glass container and a porous substrate such as, for example, a porous vascular graft, was submerged in the sealant mixture. A vacuum was applied to the glass container until no bubbles remained on the surface of the graft or in the solution. The vacuum forced the sealant into the interstitial spaces of the graft. Then, the graft was removed from the sealant mixture, excess sealant removed or squeezed out and allowed to dry.

Alternatively, the graft may be filled with a sealant composition according to the present invention and pressurized to cause penetration of the composition into the pores of the graft wall. For example, one end of a porous substrate, such as, for example, a vascular graft, was tied off. The other end of the graft was connected to the nozzle portion of a 60 cc syringe. The syringe was filled with a composition of the present invention and the composition was pushed through the syringe with a plunger. In this way, the composition of the present invention impregnated, e.g., was forced into the interstitial spaces of the graft. Once the graft was filled with the composition, the syringe was withdrawn and excess sealant was removed from the graft. The graft was then allowed to dry. This injection procedure may be repeated any number of times as may be required to ensure effective impregnation of the substrate, for example, up to six times. Other means of using force to cause sealant penetration into the interstices of the graft wall are also contemplated.

As previously described, the sol-gel of the present invention is made from a partially water-extractable, e.g., water soluble, material. The solubility rate of the sol-gel material of the present invention is, however, very low. The sol-gel material of the present invention is formed from at least two polysaccharides as described herein above. Accordingly, such a sol-gel sealant is optimally suited for providing blood-tight barriers to porous graft materials because such a sealant provides an initial blood-tight surface that is slowly biodegraded and/or solubilized into biocompatible products to permit endothelial cell proliferation into the graft from the surrounding tissue.

Gums, for example, seed gums, are polymeric substances that, in an appropriate solvent or swelling agent, form highly viscous dispersions or gels at low, dry substance content. In particular, seed gum polysaccharides are water soluble polymers that produce viscous aqueous dispersions. The seed gum polysaccharide family of the present invention includes, for example, corn starch, guar gum and locust bean gum, although other gum materials are also useful. Similarly, the sea weed extract polysaccharides are also water-soluble polymers that produce viscous aqueous dispersions. Thus, all members of the sea weed extract polysaccharide family may be used in the present invention, including, for example, algin, carrageenan, including types I–IV, and agar.

In one embodiment of the present invention, the hydrogel includes a combination of a linear polysaccharide component and a branched polysaccharide component dispersed in a glycerol-water solution. The linear polysaccharides of the present invention are water-soluble polymers that produce viscous aqueous dispersions. Thus, all members of the linear polysaccharide family may be used in the present invention, including, for example, algin, starch amylose and its derivatives, carrageenan, including types I–IV, pectin, and cellulose derivatives. Similarly, the branched polysaccharides of the present invention are water-soluble polymers that produce viscous aqueous dispersions. Thus, all members of the branched polysaccharide family may be used in the present invention, including, for example, guar gum, xanthan, locust bean gum, starch, amylopectin and its derivatives, and gum arabic.

The following examples are provided to further illustrate methods of preparation of the sealant compositions and their application to porous implantable substrates.

EXAMPLE 1

CARRAGEENAN TYPE I/LOCUST BEAN GUM

Several preparations of the sealant compositions of the present invention were prepared in 600 ml beakers as described herein.

Sealant Composition A: A solution of carrageenan type I (SIGMA Chemical Co., St. Louis, Mo.) was prepared by adding 4 gm of carrageenan type I to 300 ml of water under constant mixing with a Dyna-Mixer. The carrageenan type I used in this experiment is predominantly of the kappa variety and contains lesser amounts of the lambda variety. This carrageenan type I is of commercial grade and is derived from various seaweeds. When this solution was smooth and no lumps were visible, the mixing was stopped and 20 gm of glycerol was added thereto and then stirred by hand.

Sealant Composition B: A solution of locust bean gum was prepared by adding 3 gm locust bean gum to 300 ml water under constant mixing with a Dyna-Mixer. When this solution was smooth and no lumps were visible, the mixing was stopped and 20 gm of glycerol was added thereto and then stirred by hand.

Sealant Composition C: Equal amounts (1:1 mixture) of solutions A and B was prepared by hand mixing.

The ability of Solution C to make woven and knitted double velour grafts water-tight was then assessed under the following three conditions: (1) grafts were coated with a room temperature sealant and then dried at room temperature; (2) grafts were coated with a sealant at a temperature of 60° C. and then dried at room temperature; (3) grafts were coated with a room temperature sealant and then dried at 60° C. Each parameter was tested in triplicate. For purposes of this invention, "room temperature" means a temperature from about 22° C. to about 25° C.

To impregnate each graft with one of the sealant compositions, the following protocol was followed. Each graft was attached to a 60 cc syringe. A sealant composition was then added to the syringe and was then injected into the graft until the graft was full and under pressure. The graft was then emptied, the excess sealant removed by applying force thereto and allowed to dry. Grafts dried at room temperature were allowed to dry from about 2 to about 4 hours. Grafts dried at 60° C. were dried in an oven from about 30 minutes to about 1 hour. This procedure was repeated six times per graft. After the sixth treatment, the ability of each sealant composition to seal the graft was tested by measuring the water porosity, e.g., specific porosity, of the graft as described hereinabove. Table 3 summarizes the results for each of the grafts tested.

TABLE 3

CARRAGEENAN TYPE I/LOCUST BEAN

| GRAFT SAMPLE | GRAFT DIAMETER (cm) | GRAFT LENGTH (cm) | WATER (ml) | POROSITY** (ml/min/cm$^2$) |
|---|---|---|---|---|
| Uncoated Woven | 0.8 | 25 | 3550 | 56.5 |
| Uncoated Knitted | 0.8 | 25 | 3510 | 56.5 |
| Woven 1* | 0.8 | 27 | 200 | 3.68 |
| Woven 2+ | 0.8 | 27 | 750 | 13.80 |
| Knitted Double Velour 1* | 0.8 | 21 | 2750 | 52.10 |
| Knitted Double Velour 2+ | 0.8 | 21 | 3200 | 60.60 |

*Graft impregnated with 23° C. sealant and dried at room temperature.
+Graft impregnated with 60° C. sealant and dried at room temperature.
**Porosity measured in accordance with the Wesolowski test described herein.

As the data indicate, the sealant impregnated woven grafts were significantly more water-tight than the knitted double velour grafts. Both the woven and knitted grafts held more water when the sealant was injected at 60° C. It should be noted that all grafts were soft and flexible after the final coating and were manipulated easily without causing the sealant to crack. As the specific porosity of all of the grafts were ≧1 mi/min/cm$^2$, none of these preparations are suitable for implanting into a host organism. Accordingly, a sealant composition of carrageenan type II and locust bean gum was tried.

EXAMPLE 2

CARRAGEENAN TYPE II/LOCUST BEAN GUM

In another experiment, the sealant properties of a carrageenan type II—locust bean gum hydrogel were assessed. The protocol for this experiment was the same as in Example 1 except that in Sealant Composition A, 4 gm of carrageenan type II (SIGMA Chemical Co., St. Louis, Mo.) was used instead of carrageenan type I. The carrageenan type II used in this experiment is predominantly of the iota variety. In addition, Sealant Composition A alone was used to impregnate a woven graft. The results of the experiment are indicated below in Table 4.

TABLE 4

CARRAGEENAN TYPE II/LOCUST BEAN GUM

| GRAFT SAMPLE | GRAFT DIAMETER (cm) | GRAFT LENGTH (cm) | WATER (ml) | POROSITY** (ml/min/cm$^2$) |
|---|---|---|---|---|
| Uncoated Woven | 0.8 | 25 | 3550 | 56.5 |
| Uncoated Knitted | 0.8 | 25 | 3510 | 56.5 |
| Woven 1* | 0.8 | 27 | 6 | 0.09 |
| Woven 2+ | 0.8 | 27 | 8 | 0.12 |
| Woven 3# | 0.8 | 27 | 1 | 0.01 |
| Knitted Double Velour 1* | 0.8 | 24 | 2600 | 43.13 |
| Knitted Double Velour 2+ | 0.8 | 24 | 2650 | 43.96 |
| Knitted Double Velour 3# | 0.8 | 21 | 1050 | 19.90 |
| Woven (carrageenan type II alone)* | 0.8 | 27 | 2000 | 29.49 |
| Woven (carrageenan type II alone)# | 0.8 | 28 | 300 | 4.27 |

*Graft impregnated with 23° C. sealant and dried at room temperature.
+Graft impregnated with 60° C. sealant and dried at room temperature.
Graft impregnated with 23° C. sealant and dried at 60° C.
**Porosity measured in accordance with the Wesolowski test described herein.

As the data indicate, the sealant impregnated woven grafts were significantly more water-tight than the knitted double velour grafts. There is no difference in porosity between grafts dried at room temperature versus grafts dried at 60° C. Both the woven and knitted grafts held more water when the sealant was injected at 60° C. The woven grafts coated with carrageenan type II alone were significantly more porous than grafts coated with the carrageenan type II/locust bean mixture. Drying the carrageenan type II coated graft at 60° C. significantly improved water tightness as demonstrated in the porosity tests. All grafts were soft and flexible after the final coating and were manipulated easily without causing the sealant to crack. As the data indicate, the carrageenan type II/locust bean gum sealant impregnated woven grafts were substantially water tight, e.g., gave specific porosity data of ≦1.0 ml/min/cm$^2$. These data indicate that such a graft-sealant combination is viable for implanting into a host organism.

EXAMPLE 3

CARRAGEENAN TYPE IV/LOCUST BEAN GUM

In another experiment, the sealant properties of a carrageenan type IV/locust bean gum hydrogel were assessed. The protocol for this experiment was the same as in Example 1 except that in Sealant Composition A, 4 gm of carrageenan type IV (SIGMA Chemical Co., St. Louis, Mo.) was used instead of carrageenan type I. The carrageenan type IV used in this experiment is predominantly of the lambda variety. The carrageenan type IV used in this experiment was derived from *Gizartina aciculaire* and *G. pistillata*. The results of this experiment are indicated below in Table 5.

TABLE 5

CARRAGEENAN TYPE IV/LOCUST BEAN GUM

| GRAFT SAMPLE | GRAFT DIAMETER (cm) | GRAFT LENGTH (cm) | WATER (ml) | POROSITY** (ml/min/cm$^2$) |
|---|---|---|---|---|
| Uncoated Woven | 0.8 | 25 | 3550 | 56.5 |
| Uncoated Knitted | 0.8 | 25 | 3510 | 56.5 |
| Woven 1* | 0.8 | 27 | 5 | 0.07 |
| Woven 2+ | 0.8 | 28 | 5 | 0.07 |
| Knitted Double Velour 1* | 0.8 | 25 | 2050 | 32.60 |
| Knitted Double Velour 2+ | 0.8 | 26 | 1550 | 23.70 |

*Graft impregnated with 23° C. sealant and dried at room temperature.
+Graft impregnated with 60° C. sealant and dried at room temperature.
**Porosity measured in accordance with the Wesolowski test described herein.

As the data indicate, the sealant impregnated woven grafts were significantly more water-tight than the knitted double velour grafts. There was no difference in porosity between the woven grafts injected with 60° C. sealant compared to woven grafts injected with 23° C. sealant. The knitted grafts, however, held more water when the sealant was injected at 60° C. It should be noted that all grafts were soft and flexible after the final coating and were manipulated easily without causing the sealant to crack. As the data indicate, like the carrageenan type II/locust bean gum sealant, the carrageenan type IV/locust bean gum sealant was able to provide a substantially water-tight graft that can be implanted into a host organism.

As Examples 1–3 demonstrate, carrageenan types II and IV were more effective in sealing the grafts when used in combination with locust bean gum than carrageenan type I. The sealants were more effective when used with woven grafts than with knitted double velour grafts primarily due to the larger porosity inherent in knitted constructions. In grafts impregnated with carrageenan type II and locust bean gum, there was no difference between grafts that were dried at room temperature versus grafts dried at 60° C. Both the knitted and woven grafts injected with 60° C. sealant held more water in the porosity tests when compared to similar grafts injected with 23° C. sealant.

The woven grafts coated with carrageenan type II alone did not give comparable results to the woven grafts coated with the carrageenan type II and locust bean gum combination. The results in Table 4, however, demonstrate that the carrageenan type II impregnated grafts dried at 60° C. allowed more sealant to adhere to the graft and were less porous. Grafts coated with the carrageenan type IV/locust bean gum combination were comparable to the carrageenan type II/locust bean gum combination. The drying method did not change the observed porosity characteristics. Grafts coated with the carrageenan type I/locust bean gum combination, however, were the most porous of the sealant mixtures tested in Examples 1–3.

EXAMPLE 4

AGAR/GUAR GUM

In an attempt to find an universally applicable sealant, e.g., a sealant that renders both woven and knitted textile grafts substantially blood-tight, it was decided to experiment with a mixture including a combination of agar/guar gum. In this example, the porosity of grafts impregnated with a hydrogel made from the combination of purified agar and guar gum was tested. Two knitted grafts and two double velour grafts were injected at 60° C. because it was found that the agar/guar gum sealant mixture formed a gel at 40° C. Each graft was injected six times as described in Example 1. One of each type of graft was dried between injections at room temperature from about 1 to about 2 hours (denoted trial 1) and the other grafts were dried in an oven at 60° C. from about 30 minutes to about 1 hour (denoted trial 2). Water porosity testing was performed on each graft as described in Example 1 above. The results of the porosity testing for the purified agar/guar gum sealant composition is presented hereinbelow as Table 6.

TABLE 6

AGAR/GUAR GUM
TRIAL 1

| GRAFT SAMPLE | GRAFT DIAMETER (cm) | GRAFT LENGTH (cm) | WATER (ml) | POROSITY** (ml/min/cm$^2$) |
|---|---|---|---|---|
| Uncoated Knitted | 0.8 | 25 | 3510 | 56.5 |
| Uncoated Woven | 0.8 | 25 | 3550 | 56.50 |
| Woven 1 | 0.8 | 24 | 3 | 0.049 |
| Woven 2 | 0.8 | 24 | 3 | 0.049 |
| Knitted 1 | 0.8 | 20 | 35 | 0.696 |
| Knitted 2 | 0.8 | 19 | 165 | 3.45 |

**Porosity measured in accordance with the Wesolowski test described herein.

In another experiment, the purified agar/guar gum mixture was tested again as described above but using a different batch of knitted and double velour grafts. As indicated in Table 7 herein below, the results between the two experiments are comparable.

TABLE 7

AGAR/GUAR GUM
TRIAL 2

| GRAFT SAMPLE | GRAFT DIAMETER (cm) | GRAFT LENGTH (cm) | WATER (ml) | POROSITY** (ml/min/cm$^2$) |
|---|---|---|---|---|
| Uncoated Knitted | 0.8 | 25 | 3510 | 56.5 |
| Uncoated Woven | 0.8 | 25 | 3550 | 56.5 |
| Woven #1 | 0.8 | 20 | 1 | 0.019 |
| Woven #2 | 0.8 | 20 | 2 | 0.039 |

TABLE 7
AGAR/GUAR GUM
TRIAL 2

| GRAFT SAMPLE | GRAFT DIAMETER (cm) | GRAFT LENGTH (cm) | WATER (ml) | POROSITY** (ml/min/cm$^2$) |
|---|---|---|---|---|
| Knitted #1 | 1.0 | 16.5 | 11 | 0.212 |
| Knitted #2 | 1.0 | 16.5 | 54 | 1.04 |

**Porosity measured in accordance with the Wesolowski test described herein.

As the results from tables 6 and 7 indicate, grafts dried at room temperature were less porous than grafts dried at 60°

C. It is thought that as heat removes water from the graft it interferes with the gelling process and leads to the observed higher porosity results. In addition, the grafts dried at room temperature were more flexible than the graft dried at 60° C. The results indicate that the purified agar/guar gum sealants are comparable to the carrageenan types II and IV/locust bean gum sealant mixtures. In fact, the data from Tables 6 and 7 suggest that the agar/guar gum sealant mixture, when dried at room temperature, is well suited for rendering blood-tight both woven and knitted grafts.

EXAMPLE 5

In this example, data is provided from various porosity experiments conducted as described in Example 1. In this experiment, the porosity of knitted and woven grafts were assessed by changing various parameters including the polysaccharides used, the concentration and ratio of the various polysaccharides, the concentration of glycerol, as well as, the temperature of the sealant and of the drying process. These data are summarized in Table 8 herein below.

TABLE 8

| Sealant Components | Glycerol Content | Graft Type | Coating Method | No. Of Injections | Drying Temperature | Porosity Value (ml/min/cm³) | Comments |
|---|---|---|---|---|---|---|---|
| 1.0 Alginate/100 ml water (Graft dipped in 1% CaCl Solution after coating) | None | Knitted 12 mm | Vacuum Room Temp Sealant | — | 23° C. | Not tested | Coating Uneven, Brittle |
| 4.5 Alginate/300 ml water (Graft dipped in 1% CaCl Solution after coating) | 6 g | Knitted 8 mm | Injection Room Temp Sealant | 4 | 23° C. | 29.7 | Coating Uneven, Gelation not controlled |
| 1.0 g CarrageenanType I/200 ml water | None | Knitted 12 mm | Vaccum Room Temp Sealant | — | 23° C. | 47.4 | Coating Uneven, Stiff, Brittle |
| 1.0 g Locust Bean Gum/200 ml water | 16.8 g 16.8 g = 33.6 g Total | Knitted 12 mm | Vacuum Room Temp Sealant | — | 23° C. | 48.8 | Graft flexible, not coated in crimps |
| 4.5 g Carrageenan Type I/300 ml water | 4.5 g 3.0 g | Knitted 12 mm | Vaccum Room Temp Sealant | — | 23° C. | 47.7 | Coating on graft broke under pressure of porometer |
| 3.0 g Locust Bean Gum/300 ml water | = 7.5 g Total | Knitted 12 mm | Vacuum 50° C. Sealant | — | 23° C. | 47.7 | Coating on graft broke under pressure of porometer |
| 5.0 Carrageenan Type I/300 ml water | 40 g 40 g = 80 Total | Knitted 12 mm | Injection Room Temp Sealant | 4 | 23° C. | 47.1 | Grafts were very oily |
| 4.0 g Carrageenan Type I/300 ml water | 30 g 30 g | Woven 8 mm | Injection Room Temp Sealant | 6 | 23° C. | 3.68 | — |
| 3.0 g Locust Bean Gum | = 60 g Total | Woven 8 mm | Injection Rootn Temp Sealant | 6 | 60° C. | 13.8 | — |
|  |  | Knitted 8 mm | Injection Room Temp Sealant | 6 | 23° C. | 52.10 | — |
|  |  | Knitted 8 mm | Injection Room Temp Sealant | 6 | 60° C. | 60.60 | — |
| 4.0 g Carrageenan Type II/300 ml water | 20 g 20 g = 40 g Total | Woven 8 mm | Injection Room Temp Sealant | 3 | 23° C. | 37.3 | — |
|  |  | Woven 8 mm | Injection Room Temp Sealant | 4 | 23° C. | 32.2 | — |
| 4.0 g Carrageenan Type II/300 ml water | 30 g 30 g = 60 g Total | Woven 8 mm | Injection Room Temp Sealant | 6 | 23° C. | 0.068 | First woven graft to give porosity value less than 1.0. |
|  |  | Woven 8 mm | Injection 60° C. Sealaat | 6 | 23° C. | 0.064 | — |
|  |  | Woven 8 mm | Injection Room Temp. Sealant | 6 | 60° C. | 0.102 | — |
| 4.0 g. Carrageenan Type II/300 ml water | 30 g 30 g = 60 g Total | Woven 8 mm | Injection Room Temp Sealant | 6 | 23° C. | 0.088 | — |
| 3.0 g. Locust Bean Gum/300 ml. water (Retrials) |  | Woven 8 mm | Injection 60° C. Sealant | 6 | 23° C. | 0.014 | — |
|  |  | Woven 8 mm | Injection Room Temp Sealant | 6 | 60° C. | 0.118 | — |
|  |  | Knitted 8 mm | Injection Room Temp Sealant | 6 | 23° C. | 43.1 | — |
|  |  | Knitted | Injection | 6 | 23° C. | 19.9 | — |

TABLE 8-continued

| Sealant Components | Glycerol Content | Graft Type | Coating Method | No. Of Injections | Drying Temperature | Porosity Value (ml/min/cm³) | Comments |
|---|---|---|---|---|---|---|---|
| 4.0 g Carrageenan Type II | 30 g | 8 mm Knitted | 60° Sealant Injection | 6 | 60° C. | 44.0 | — |
| | | 8 mm Woven | Room Temp Sealant Injection | 6 | 23° C. | 29.5 | — |
| | | 8 mm Knitted | Room Temp Sealant Injection | 6 | 60° C. | 4.27 | — |
| | | 8 mm Woven | Room Temp Sealant Injection | 6 | 23° C. | 0.015 | Coated Graft slightly inflexible |
| 8.0 g Carrageenan Type II/300 ml water | 30 g | 8 mm Woven | Room Temp Sealant Injection | 4 | 23° C. | 0.015 | Coated Graft slightly inflexible |
| 6.0 g Locust Bean Gum | 30 g = 60 g Total | 8 mm Woven | Room Temp Sealant Injection | 5 | 23° C. | 0.015 | Coated Graft slightly inflexible |
| | | 8 mm Knitted | Room Temp Sealant Injection | 6 | 23° C. | 3.86 | Coated Graft too Stiff |
| | | 8 mm Knitted | Room Temp Sealant Injection | 6 | 60° C. | 2.62 | Coated Graft too Stiff |
| | 45 g | 8 mm Woven | Room Temp Sealant Injection | 6 | 23° C. | 4.37 | Coated graft Flexible |
| | 45 g = 90 g Total | 8 mm Knitted | Room Temp Sealant Injection | 6 | 60° C. | 1.46 | Coated graft Flexible |
| 2.0 g Carrageenan Type IV/150 ml water | 15 g | 8 mm Woven | Injection | 6 | 23° C. | 0.07 | — |
| 1.5 g. Locust Bean Gum/150 ml water | 15 g = 30 g Total | 8 mm Knitted | Rooin Temp Sealant Injection | 6 | 60° C. | 0.07 | — |
| | | 8 mm Knitted | Injection | 6 | 23° C. | 32.6 | — |
| | | 8 mm Woven | Room Temp Sealant Injection | 6 | 60° C. | 23.70 | — |
| 8.0 g Carrageenan Type IV/300 ml water | 60 g | 8 mm Woven | Injection | 6 | 23° C. | Not Tested | Grafts felt very oily. Glycerol content too high. |
| 6.0 g Locust Bean Gum/300 ml water | 60 g = 120 g Total | 8 mm Knitted | Room Temp Sealant Injection | 6 | 60° C. | Not Tested | Grafts felt very oily. Did not completely dry. Glycerol content too high. |
| | | 8 mm Woven | Injection | 6 | 23° C. | 19.9 | Grafts felt very oily. Glycerol content too high. |
| | | 8 min Knitted | Room Temp Sealant Injection | 6 | 60° C. | 25.8 | Grafts felt very oily. Glycerol content too high. |
| | 32 g | 8 mm Knitted | Injection | 6 | 23° C. | 0.0468 | First knitted graft to give porosity level less than 1.0 |
| | 46 g = 78 g Total | 8 mm Woven | Room Temp Sealant Injection | 6 | 60° C. | 0.248 | — |
| 8.0 g Carrageenan Type IV/300 ml water | 35 g | 8 mm Knitted | Injection | 6 | 23° C. | 0 | Graft did not leak any water in porosity test |
| 8.0 g Guar Gum/300 ml water | 35 g = 70 g Total | 8 mm Woven | Room Temp Sealant Injection | 6 | 60° C. | 0 | Graft did not tesk any water in porosity test |
| | | 8 mm Knitted | Injection | 6 | 23° C. | 0.942 | — |
| | | 8 mm Room Temp Sealant | | | | | |

TABLE 8-continued

| Sealant Components | Glycerol Content | Graft Type | Coating Method | No. Of Injections | Drying Temperature | Porosity Value (ml/min/cm³) | Comments |
|---|---|---|---|---|---|---|---|
| 3.0 g Purified Agarose/300 ml water (Heated to 90° C. to dissolve) | 30 g Total | Knitted 8 mm | Injection Room Temp Sealant | 6 | 60° C. | 0.610 | — |
| | | Woven 8 mm | Injection 60° C. Sealant | 6 | 23° C. | 0.049 | — |
| | Woven | Injection 8 min | 6 | 60° C. | 0.049 | — | |
| 6.0 g Guar Gum/300 ml water | | Knitted 8 mm | Injection 60° C. Sealant | 6 | 23° C. | 0.0696 | — |
| | | Knitted 8 mm | Injection 60° C. Sealaat | 6 | 60° C. | 3.45 | — |
| | | Woven 8 mm | Injection 60° C. Sealant | 6 | 23° C. | 0.019 | — |
| | | Woven 8 mm | Injection 60° C. Sealant | 6 | 60° C. | 0.039 | — |
| | | Knitted 8 mm | Injection 60° C. Sealant | 6 | 23° C. | 0.212 | — |
| | | Knitted 8 min | Injection 60° C. Sealant | 6 | 60° C. | 1.04 | — |
| 5.0 g Chitosan/300 ml 0.1 M Acetic Acid | 30 g | Woven 7 mm | Injection Room Temp Sealant | 6 | 23° C. | 0 | — |
| 7.0 g Guar Gum/300 ml water | 30 g | Woven 7 mm | Injection Room Temp Sealant | 6 | 60° C. | 0.021 | — |
| | | Knitted 7 mm | Injection Room Temp Sealant | 6 | 23° C. | 0.162 | — |
| | | Knitted 7 mm | Injection Room Temp Sealant | 6 | 60° C. | 0.032 | — |

Uncoated Graft Porosity Values:
Woven 8 mm 56.5 ml/min/cm²
Knitted 8 mm 56.5 ml/min/cm²

These data indicate that sealant mixtures of carrageenan type IV/guar gum, carrageenan type IV/locust bean gum, agarose/guar gum and chitosan/guar gum sealant combinations are universally able to provide substantially blood-tight barriers to both woven and vascular grafts.

The invention being thus described, it will be obvious that the same may be varied in many ways. Such variations are not to be regarded as a departure from the spirit and scope of the invention and all such modifications are intended to be included within the scope of the following claims.

What is claimed is:

1. An implantable liquid-tight tubular prosthesis comprising:
   inner and outer porous walls, said walls having a porosity which is conducive to tissue ingrowth, said walls further being impregnated with a hydrogel comprising in combination at least two polysaccharides which interact to form a stable bioresorbable liquid tight sealant throughout said tubular prosthesis.

2. The prosthesis as in claim 1 wherein said polysaccharides are selected from the group consisting of algin, carboxymethyl cellulose, carrageenan, furcellaran, agarose, guar, locust bean gum, gum arabic, hydroxyethyl cellulose, hydroxypropyl cellulose, methyl cellulose, hydroxyalkylmethyl cellulose, pectin, partially deacetylated chitosan, starch and starch derivatives including, amylose and amylopectin, xanthan, casein, polylysine, hyaluronic acid and its derivatives, heparin, their salts, and mixtures thereof.

3. The prosthesis as in claim 1 wherein said walls are woven, knitted, extruded or casted.

4. The prosthesis as in claim 1 wherein said walls comprise at least one polymer selected from the group consisting of natural and synthetic polymers.

5. The prosthesis as in claim 1 wherein said walls comprise at least one material selected from the group consisting of polyester, expanded poly(tetrafluoroethylene), nylon, polypropylene, polyurethane and polyacrylonitrile.

6. The prosthesis of claim 1 wherein said combination of at least two polysaccharides is selected from the group of paired hydrogel polysaccharides consisting of alginic acid/pectin, alginic acid/chitosan, carrageenan type I/locust bean gum, carrageenan type I/pectin, carrageenan type II/locust bean gum, carrageenan type II/pectin, carrageenan type II/guar gum, carrageenan type IV/locust bean gum, locust bean gum/xanthan, guar gum/locust bean gum, guar gum/xantham, and agar/guar gum.

7. The prosthesis as in claim 1 wherein said at least two polysaccharides includes carrageenan type II, $Ca^{+2}$ ion and locust bean gum.

8. The prosthesis as in claim 1 wherein said at least two polysaccharides includes carrageenan type IV, $Ca^{+2}$ ion and locust bean gum.

9. The prosthesis as in claim 1 wherein said at least two polysaccharides includes purified agarose and guar gum.

10. The prosthesis as in claim 1 wherein said at least two polysaccharides includes chitosan and guar gum.

11. The prosthesis as in claim 1 wherein an anticoagulant agent is incorporated into said hydrogel, said hydrogel controllably releasing said anticoagulant through said porous walls.

12. The prosthesis as in claim 11 wherein said anticoagulant agent is selected from the group consisting of heparin, prostaglandin, urokinase, streptokinase, sulfated polysaccharide, albumin, their pharmaceutical salts and mixtures thereof.

13. The prosthesis of claim 1 wherein said at least two polysaccharides are heparin and chitosan, respectively.

14. The prosthesis as in claim 1 wherein said polysaccharides are cross-linked.

15. A controlled-release bioresorbable sealant composition for use in soft tissue prostheses comprising:
   a hydrogel matrix,
   a bio-active agent incorporated therein, said hydrogel comprising in combination at least two polysaccharides which when combined in an aqueous medium interact to form said hydrogel and which when impregnated into a porous soft-tissue prosthesis provides a liquid-tight seal.

16. An implantable soft tissue prosthesis which comprises:
   a tubular member having inner and outer porous walls for tissue ingrowth, said prosthesis impregnated with a bioresorbable hydrogel sealant, said bioresorbable hydrogel sealant including in combination a seed gum polysaccharide and a sea weed extract polysaccharide dispersed in a glycerol-water solution.

17. A method for rendering an implantable soft tissue porous substrate fluid-tight comprising:
   a. providing said implantable soft tissue porous substrate having inner and outer surfaces and a porosity defined by pores in said surfaces;
   b. impregnating said surfaces with a hydrogel defined by at least two polysaccharides to fill said pores with said hydrogel;
   c. allowing said hydrogel to form a seal in said pores rendering said substrate liquid-tight.

18. A method for rendering an implantable soft tissue porous substrate fluid-tight comprising:
   a. providing said implantable soft tissue porous substrate having inner and outer surfaces and a porosity defined by pores in said surfaces;
   b. impregnating said surfaces with a sol-gel defined by at least two polysaccharides to fill said pores with said sol-gel;
   c. allowing said sol-gel to form a seal in said pores rendering said substrate liquid-tight.

19. An implantable soft tissue prosthesis that comprises:
   a tubular member having inner and outer porous walls for tissue ingrowth, said member impregnated with a bioresorbable hydrogel sealant, said bioresorbable hydrogel sealant comprising in combination a linear polysaccharide component and a branched polysaccharide component dispersed in a glycerol-water solution.

* * * * *

UNITED STATES PATENT AND TRADEMARK OFFICE
CERTIFICATE OF CORRECTION

PATENT NO. : 5,851,229
DATED : December 22, 1998
INVENTOR(S) : Lentz, et al.

It is certified that error appears in the above-identified patent and that said Letters Patent is hereby corrected as shown below:

Column 11, Line 56, "made into yams", should read -- made into yarns--;

Column 12, Line 18, now reads "additional yams", should read -- additional yarns--.

Signed and Sealed this

Fourth Day of May, 1999

Q. TODD DICKINSON

*Attest:*

*Attesting Officer*   Acting Commissioner of Patents and Trademarks